(12) United States Patent
Lowery et al.

(10) Patent No.: US 9,289,141 B2
(45) Date of Patent: Mar. 22, 2016

(54) APPARATUS AND METHODS FOR THE MEASUREMENT OF CARDIAC OUTPUT

(75) Inventors: Guy Russell Lowery, San Juan Capistrano, CA (US); William J. Grande, Pittsford, NY (US)

(73) Assignees: Micropen Technologies Corporation, Honeoye Falls, NY (US); Ecom Med., Inc., San Juan Capistrano, CA (US)

(*) Notice: Subject to any disclaimer, the term of this patent is extended or adjusted under 35 U.S.C. 154(b) by 1184 days.

(21) Appl. No.: 12/249,886

(22) Filed: Oct. 10, 2008

(65) Prior Publication Data

US 2009/0227885 A1 Sep. 10, 2009

Related U.S. Application Data

(60) Provisional application No. 60/998,682, filed on Oct. 12, 2007.

(51) Int. Cl.
*A61B 5/02* (2006.01)
*A61B 5/029* (2006.01)
*A61B 5/053* (2006.01)
*A61B 5/00* (2006.01)
(Continued)

(52) U.S. Cl.
CPC .............. *A61B 5/029* (2013.01); *A61B 5/0535* (2013.01); *A61B 5/0538* (2013.01); *A61B 5/6853* (2013.01); *H05K 1/117* (2013.01);
(Continued)

(58) Field of Classification Search
CPC ............ A61B 5/00; A61B 5/02; A61B 5/024; A61B 5/0255; A61B 5/026; A61B 1/00; A61B 1/267; A61B 1/313; A61B 5/01; A61B 5/0205; A61B 5/021; A61B 5/0215; A61B 5/022; A61B 5/0245; A61B 5/0265; A61B 5/04
See application file for complete search history.

(56) References Cited

U.S. PATENT DOCUMENTS 3,326,207 A 6/1967 Egan
4,967,759 A * 11/1990 Teves ............................ 600/528
(Continued)

FOREIGN PATENT DOCUMENTS

WO WO-2004016438 A1 2/2004
WO WO-2006105121 A2 10/2006

OTHER PUBLICATIONS

Pieper CF, Lawrie G, Parsons D, Lacy J, Roberts R, and Pacifico A: "Experience with Kapton-Based Bipolar Electrode Arrays Used During Computerized Intraoperative Mapping" J Cardiovasc Electrophysiol, 12 pgs.
(Continued)

*Primary Examiner* — Christopher D Koharski
*Assistant Examiner* — Elizabeth K So
(74) *Attorney, Agent, or Firm* — LeClairRyan, a Professional Corporation (57) ABSTRACT

The current invention provides an endotracheal tube fabricated with an array of electrodes disposed on an inflatable cuff on the tube. The array of electrodes includes multiple sense electrodes and a current electrode. The array of electrodes on the inflatable cuff is applied using a positive displacement dispensing system, such as a MicroPen®. A ground electrode is disposed on the tube approximately midway between the inflatable cuff and the midpoint of the endotracheal tube. The endotracheal tube is partially inserted into a mammalian subject's airway such that when the inflatable cuff is inflated, thereby fixing the tube in position, the array of electrodes is brought into close contact with the tracheal mucosa in relative proximity to the aorta. The endotracheal tube is useful in the measurement of cardiac parameters such as cardiac output.

14 Claims, 4 Drawing Sheets

(51) Int. Cl.
  *H05K 1/11* (2006.01)
  *A61B 5/042* (2006.01)
  *H05K 1/02* (2006.01)
  *H05K 1/14* (2006.01)
  *H05K 3/40* (2006.01)

(52) U.S. Cl.
  CPC ...... *A61B 5/0421* (2013.01); *A61B 2562/0209* (2013.01); *A61B 2562/046* (2013.01); *A61B 2562/125* (2013.01); *H05K 1/0284* (2013.01); *H05K 1/141* (2013.01); *H05K 1/147* (2013.01); *H05K 3/4069* (2013.01); *H05K 2201/0949* (2013.01)

(56) References Cited

U.S. PATENT DOCUMENTS

| | | |
|---|---|---|
| 5,311,863 A | 5/1994 | Toppses et al. |
| 5,928,571 A | 7/1999 | Chan |
| 6,273,875 B1 | 8/2001 | Siman et al. |
| 6,292,689 B1 | 9/2001 | Wallace et al. |
| 6,401,001 B1 | 6/2002 | Jang et al. |
| 7,211,205 B2 | 5/2007 | Conaghan et al. |
| 2001/0017085 A1 | 8/2001 | Kubo et al. |
| 2001/0019340 A1 | 9/2001 | Kubo et al. |
| 2003/0100824 A1 | 5/2003 | Warren et al. |
| 2004/0253185 A1 | 12/2004 | Herweck et al. |
| 2006/0095032 A1 | 5/2006 | Jackson et al. |
| 2006/0118121 A1 | 6/2006 | Martens et al. |
| 2008/0039709 A1* | 2/2008 | Karmarkar .................. 600/410 |

OTHER PUBLICATIONS

European Patent Office, The International Search Report and Written Opinion of the International Searching Authority, dated Jul. 2, 2009, 25 pgs.

* cited by examiner

APPARATUS AND METHODS FOR THE MEASUREMENT OF CARDIAC OUTPUT

RELATED APPLICATIONS

This application claims the benefit of priority to U.S. Provisional Application No. 60/998,682, filed Oct. 12, 2007, the teachings of which are incorporated herein by reference in their entirety.

FIELD OF THE INVENTION

The invention provides an apparatus for measuring cardiac output in a mammalian subject. The apparatus includes a tube and an inflatable cuff and is configured so that electrodes on the inflatable cuff located in close proximity to the subject's aorta measure voltage changes following stimulation of the tissue with a current delivered by an electrode. The electrodes are printed on the tube and the cuff with a positive displacement dispensing system to improve the durability of the apparatus.

BACKGROUND OF THE INVENTION

Cardiac output is a calculation of the volume of blood being pumped by the heart, for example a ventricle, per minute. Cardiac output is equivalent to the heart rate multiplied by the stroke volume. Understanding of a subject's cardiac output is important in care of acutely injured or ill subjects, as well as individuals with chronic cardiac pathology. Until recently the standard of cardiac output measurement has been pulmonary artery catheterization. See, e.g., U.S. Pat. Nos. 3,915,155; 3,726,269 and 3,651,318.

Bioelectrical impedance analysis ("BIA") has been developed to measure physiological and pathological properties, including cardiac output. In performing BIA, a low level electrical alternating current is introduced into a tissue being monitored electrically by multiple electrodes, such that the voltage difference between multiple locations on the tissue is determined. From this determination, the electrical impedance (electrical resistance plus reactance) of the stimulated tissue is calculated. Previously, both external (U.S. Pat. No. 4,870,578) and internal (U.S. Pat. Nos. 4,852,580 and 4,836, 214) electrodes have been employed to measure electrical resistance representing blood flow in the aorta. While these internal electrodes were mounted on esophageal catheters, it was later determined that endotracheal tubes could be adapted by the addition of electrodes on the inflatable cuff, which was perceived to be a more accurate measurement of cardiac output. See U.S. Pat. Nos. 6,095,987 and 6,292,689.

The process of inserting an endotracheal tube is called intubation, and is performed\\\ when the inflatable cuff is deflated. The presence of electrodes on the inflatable cuff and electrode leads on the external surface of the endotracheal tube results in a more complex and riskier intubation process. Further, the electrodes are attached to the inflatable cuff when inflated, resulting in irregularities (e.g., sharp edges of the electrode, broken electrode leads) when the cuff is deflated prior to insertion.

In view of the foregoing, it would be desirable to provide an apparatus and methods for safely, accurately, efficiently and continuously determining cardiac output by measuring electrical impedance.

SUMMARY OF THE INVENTION

In general, aspects of the present invention relate to detection of cardiac output, and diseases characterized by abnormal cardiac function, using a novel apparatus that is placed in such a manner that a portion of the apparatus contacts the tracheal tissue in close proximity to the aorta.

In one aspect, the invention provides an apparatus that includes a tube having a proximal portion and a distal portion, an inflatable cuff, a ground electrode, a plurality of sense electrodes, and a current electrode. Generally, each sense electrode and the current electrode contains an electrode patch operably linked to a generally linear electrode runner; the sense electrodes and the current electrode are disposed on the inflatable cuff and the distal portion of the tube, and the portion of each of the electrode runners disposed on the inflatable cuff forms a beam-like structure. In certain embodiments, the portion of the electrode runner disposed on the tube extends in a generally linear proximal-distal direction along the tube and is not substantially curved. Additionally, the circumferential distance between adjacent beam-like structures is greater at the region of the inflated inflatable cuff wherein maximal outer diameter of the cuff is achieved than at the region where the inflatable cuff contacts the distal portion of the tube. In some embodiments the apparatus also includes a tubule for inflating the inflatable cuff.

The apparatus includes sense electrodes and a current electrode that are separated from the inflatable cuff by a polymeric underlayer that is applied to the inflatable cuff and the tube prior to application of the sense electrodes and the current electrode. The apparatus also includes a polymeric overlayer that contacts a portion of the electrode patch and the entirety of the electrode runner, and the polymeric overlayer is applied to the electrode after application of the electrode to the tube and cuff. In certain embodiments the polymeric underlayer contains a medical grade adhesive, such as a urethane oligomer/acrylate monomer blend (e.g., Dymax® 1-20323 resin, Torrington, Conn.) the electrode contains electrically conductive silver particles suspended in a resin and a volatile solvent that forms a polymeric matrix material once cured (such as Creative Materials—CMI 101-59), or the polymeric overlayer contains a medical grade adhesive, such as a urethane oligomer/acrylate monomer blend (e.g., Dymax® 1-20323 resin).

The apparatus includes a collection of at least three sense electrodes, and may be three, four, five or more than five sense electrodes. For example, the combination of the five sense electrodes provides three orthogonal pairs of sense electrodes. The tube of the apparatus may be an endotracheal tube. Also, the current electrode is disposed on the distal portion of the tube between the termini of the electrode runners (near the middle of the tube in a proximal-distal direction) and the inflatable cuff. In certain embodiments, the current electrode is at least one centimeter in length (e.g., one, two or more centimeters) as measured in the proximal-distal dimension of the tube. In some embodiments the current electrode extends over about 90°, 120°, or about 180° of the circumference of the tube. Optionally, the ground electrode is also placed on the tube.

In another aspect, the invention provides a method of fabricating an apparatus by providing an apparatus having a first portion and a second portion that is capable of being inflated, at least partially inflating the second portion, imaging the inflated second portion so as to obtain imaging data, directing a positive displacement dispensing system to apply to a region of the inflated second portion a polymeric underlayer based upon the imaging data, applying to at least a portion of the polymeric underlayer a conductive material based upon the imaging data, and applying to a portion of the conductive material a polymeric overlayer based upon the imaging data. In certain embodiments, no polymeric overlayer is applied to a plurality of regions of the conductive material, thereby forming a plurality of electrode patches. The imaging step comprises capturing images, such as dynamic video images. The imaging step includes in certain embodiments the capturing of a plurality of images that are used to identify one or more contours of the second portion.

In certain embodiments, one or more of the polymeric underlayer, the conductive material, or the polymeric overlayer are applied by a positive displacement dispensing system. The positive displacement dispensing system includes a pen tip that is kept substantially perpendicular to the surface of the second portion during application of the polymeric underlayer, the conductive material, or the polymeric overlayer.

In some embodiments, the apparatus is mounted on a stage having at least three independent axes of motion relative to the pen tip. For example, the apparatus is mounted on a stage having at least four independent axes of motion relative to the pen tip: motion along a direction perpendicular to the pen tip, motion along a direction towards or away from the pen tip, rotational motion along an axis perpendicular to the pen tip, and rotational motion along an axis parallel to the pen tip. In other embodiments, the positive displacement dispensing system includes a MicroPen® (MicroPen Technologies Honeoye Falls, N.Y.).

In a further aspect, the invention provides a method of fabricating an endotracheal tube by providing a tube having a proximal portion and a distal portion and an inflatable cuff disposed on the distal portion of the tube, at least partially inflating the cuff, imaging the inflated cuff so as to obtain imaging data, directing a positive displacement dispensing system to apply a polymeric underlayer to a region of the inflated cuff and a region of distal portion of the tube based upon the imaging data, applying to at least a portion of the polymeric underlayer a conductive material to form a plurality of electrodes where at least a portion of the region to which the conductive material is applied is based upon the imaging data, and applying to a portion of the conductive material a polymeric overlayer where at least a portion of the region to which the polymeric overlayer is applied is based upon the imaging data, and where no polymeric overlayer is applied to a plurality of regions of the conductive material to form a plurality of electrode patches. In some embodiments, the positive displacement dispensing system comprises a MicroPen®.

In yet another aspect, the invention provides an apparatus produced by a process containing the steps of providing a tube having a proximal portion and a distal portion, and an inflatable cuff disposed on the distal portion of the tube, at least partially inflating the cuff, imaging the inflated cuff so as to obtain imaging data, directing a positive displacement dispensing system to apply to a region of the inflated cuff a polymeric underlayer based upon the imaging data, applying to at least a portion of the polymeric underlayer a conductive material to form a plurality of electrodes based upon the imaging data, and applying to a portion of the conductive material a polymeric overlayer based upon the imaging data, and where no polymeric overlayer is applied to a plurality of regions of the conductive material so as to form a plurality of electrode patches.

In another aspect, the invention provides a method of applying a material to a non-repeatably formed substrate by providing a positive displacement dispensing system containing a pen tip, mounting the substrate on a stage having four independent axes of motion relative to the pen tip, imaging the substrate by capturing still or video images so as to obtain imaging data, and directing the positive displacement dispensing system to apply to at least a region of the substrate a material based upon the imaging data. The independent axes of motion include motion along a direction perpendicular to the pen tip, motion along a direction towards or away from the pen tip, rotational motion along an axis perpendicular to the pen tip, and rotational motion along an axis parallel to the pen tip.

In certain aspects, the imaging data are processed so as to generate a three-dimensional representation of the substrate, and the pen tip is kept at an angle substantially perpendicular to the region of the substrate to which the material is being applied.

Unless otherwise defined, all technical and scientific terms used herein have the same meaning as commonly understood by one of ordinary skill in the art to which this invention belongs. Although methods and materials similar or equivalent to those described herein can be used in the practice or testing of aspects of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

DESCRIPTION OF THE DRAWINGS AND FIGURES

The present invention may be further appreciated with reference to the appended drawing sheets wherein.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

In some embodiments described herein, the present invention relates generally to an apparatus useful as an endotracheal tube (also known as an intratracheal tube or ET tube). The endotracheal tube is useful in measuring physiological characteristics of a mammalian subject, particularly human subjects suffering from acute or chronic injury or illness. For example, the endotracheal tube is used to measure cardiac output in a mammalian subject. The endotracheal tube is inserted into the trachea, generally via the mouth, but sometimes through the nares of the nose or even through a tracheostomy.

Figure 1:
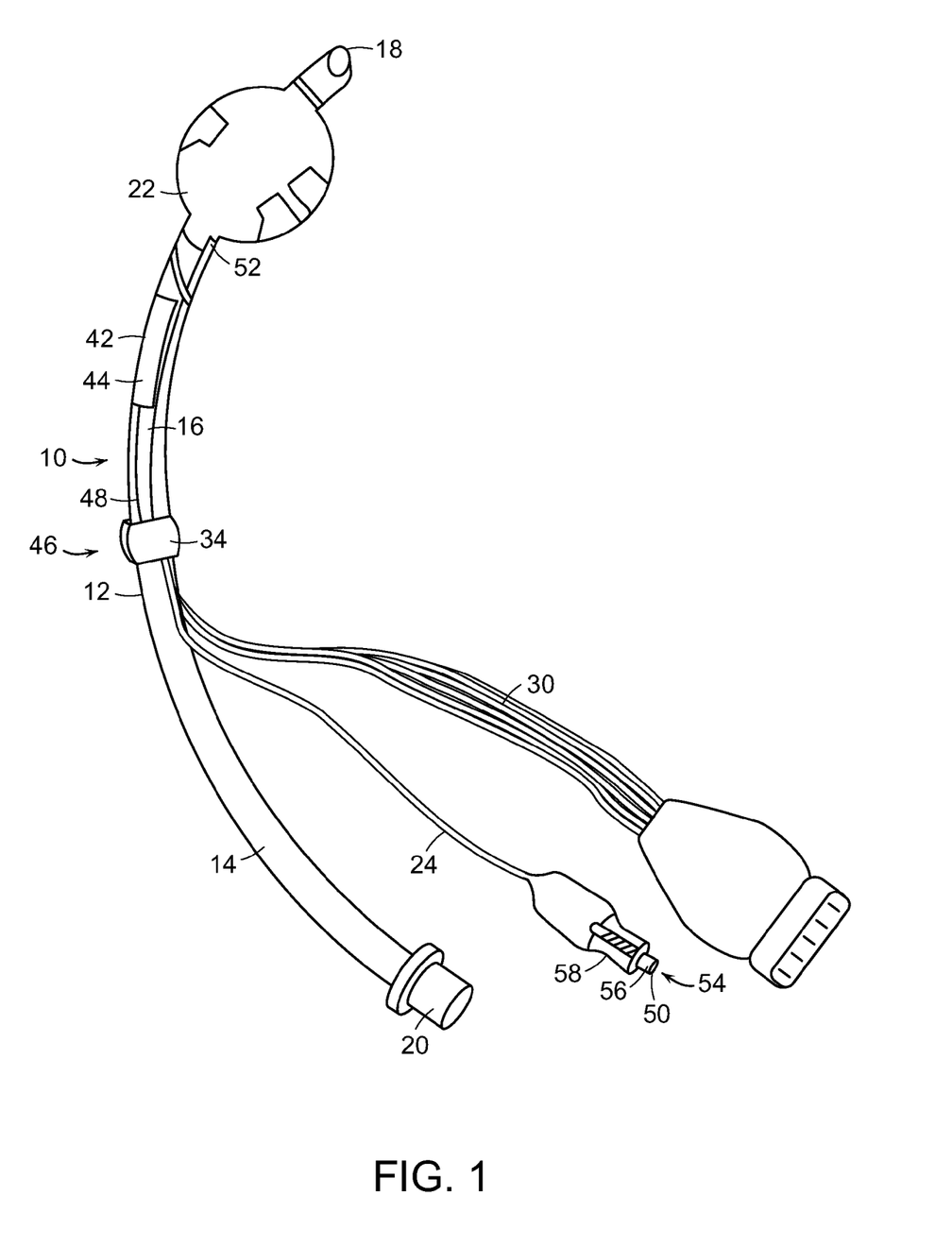
FIG. 1 is a schematic illustration demonstrating one embodiment of the endotracheal tube of the present invention.

The apparatus 10 for measuring a mammalian subject's cardiac output shown in FIG. 1 contains tube 12 having proximal portion 14 and distal portion 16. The tube 12 is generally formed of a medically approved synthetic polymeric material such as silicone rubber, polyvinyl chloride or polypropylene.

See, U.S. Pat. Nos. 3,599,642 and 4,593,690, the contents of which are incorporated herein by reference in their entireties. The distal portion 16 is inserted into the subject during the intubation, and generally has a beveled end with a smooth, curved distal tip 18 to facilitate insertion. The proximal portion 14 of the tube 12 contains a coupler member 20 that is suited to be connected to medical equipment such as a ventilator. Connected to the distal portion 16 is an inflatable cuff 22 that, when inflated, causes occlusion of the airway surrounding the apparatus 10, thereby fixing the tube in correct position while allowing the ventilator to completely regulate the patient's respiration. Generally the inflatable cuff 22 is fully deflated when it is inserted into the subject's airway in order to reduce the risk of injury to the subject during intubation. Inflation and deflation of the cuff 22 are controlled through a small secondary tubule 24 that is inserted at the proximal end of the tube.

The apparatus 10 also includes several electrodes 26, 28 operably joined to the distal portion of the tube and the inflatable cuff. The electrode contains two principal features: an electrode patch 26 that is generally rectangular and is disposed on the outer surface of the inflatable cuff, and an electrode runner 28 that is extends in a proximal-distal orientation between the electrode patch and the point where the electrode runners terminate and are attached to the bundle or sheath of external wires 30. The collection of external wires 30 is also termed a flexible circuit or flex circuit. Generally the electrode runners terminate near the middle of the tube in a proximal-distal orientation. In certain embodiments the electrode patch 26 has a rectangular (e.g., square) shape, but it should be recognized that the present invention provides for any shape of electrode patch that can be fabricated using the methods described herein and the teachings of the art (e.g., circle, oval, or any polyhedra such as triangle, pentagon, hexagon, heptagon, or octagon). The electrode patch 26 is connected to the electrode runner 28 at a corner or side of the electrode patch 26. The electrode patch can include a triangularly-shaped conductive material 32 that interfaces with the electrode patch 26 and electrode runner 28.

Figure 3A:
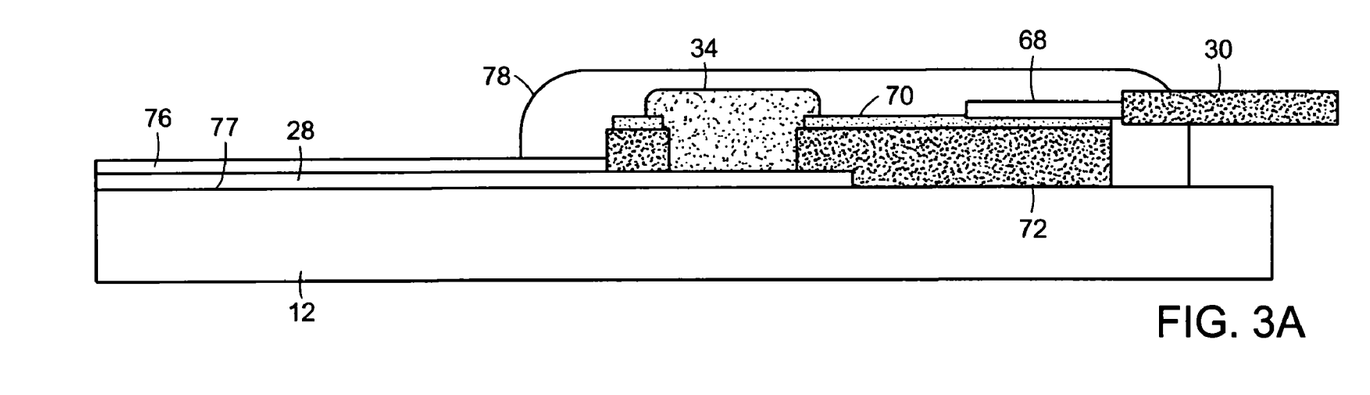
FIG. 3 is a partial sectional illustration of an electrical assembly of the present invention.
Figure 3B:
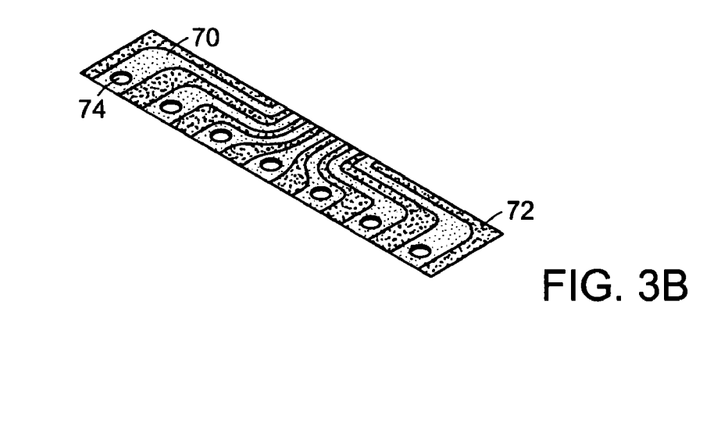

In certain embodiments of the invention the electrode runners 28 and the external wires 30 are connected using a conductive compound. An exemplary embodiment of the connection between the electrode runners 28 and the external wires 30 is schematically depicted in FIGS. 3A and 3B. The external wires 30 terminate at an end 68 not surrounded by any insulating sheath, but is connected to a traced conductive circuit material 70 operably linked to a flexible support material 72. The flexible support material 72 is any suitable material having the properties of being thin and flexible, such as a polyimide or polyamide material (e.g., a Kapton® polyimide film by DuPont). The traced conductive circuit material 70 and the flexible support material 72 contain a series of holes 74. After the electrode runners 28 are printed on the tube 12 the traced conductive circuit material 70 and the flexible support material 72 are applied over the termini of the electrode runners 28, such that the holes 74 align with the proximal end of each electrode runner 28. A conductive polymeric material 34 (such as Conductive Compounds® EP-600 epoxy resin, Londonderry, N.H.) is applied so as to fill or partially fill holes 74 and thereby form an electrical connection between electrode runner 28 and external wires 30. Optionally, the conductive polymeric material 34 is cured, such as by placing the apparatus in a container heated to a temperature of about 110° C. for a period of time from about ten minutes to about two hours. An insulating material 78 is applied over the connection between the electrode runner 28 and the external wires 30. Insulating material 78 is a sealing tape, a molded sealing collar or any medically-acceptable polymeric material, such as a two-stage medical epoxy (e.g., Loctite® M-121HP epoxy, Henkel Corporation) that protects the electrodes from bodily fluids and thereby increases the durability of the device.

The spacing between the ends of the electrode runners 28 to which the external wires 30 are connected is a consideration. It is generally preferable to have a space of at least about one millimeter between adjacent ends of the electrode runners 28. This spacing prevents the build-up of any capacitance between adjacent ends. Also, this spacing also reduces the risk of a high potential electrical failure.

Figure 2:
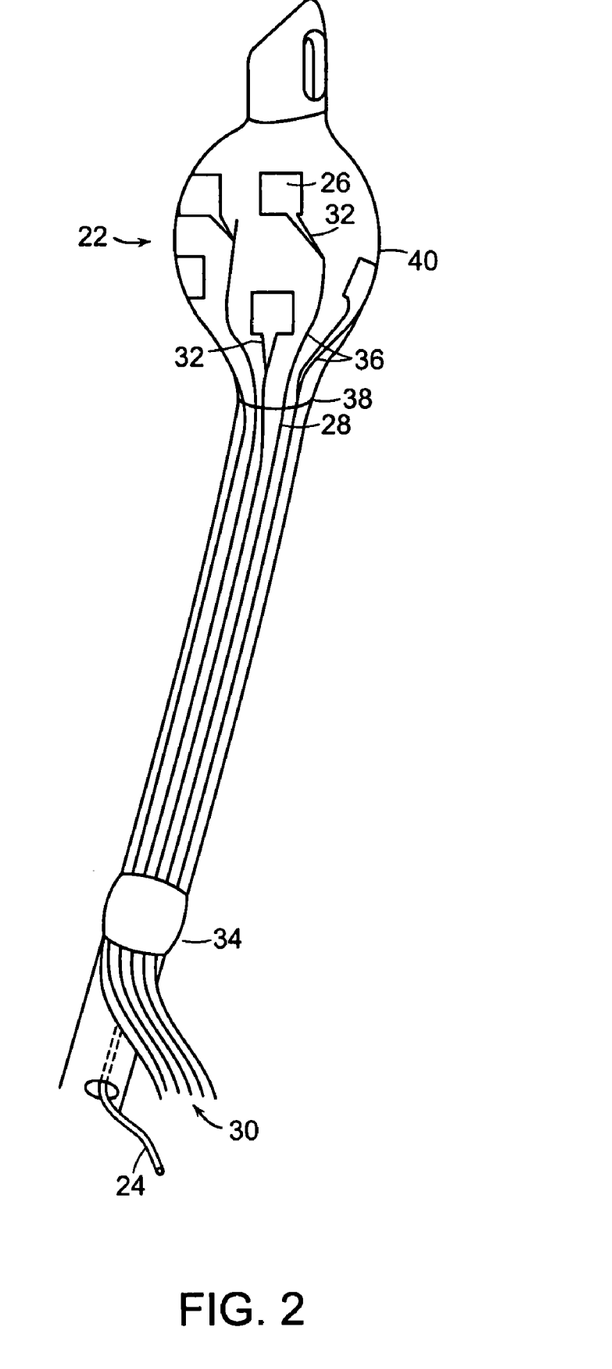
FIG. 2 is a partial sectional illustration of the endotracheal tube of the present invention.

In several embodiments of the invention, a plurality of electrodes is disposed on the inflatable cuff 22. The placement of the electrode patches 26 is dictated to some extent by the opportunity to maximize the detection and measurement of voltages caused by the current flowing in the tissue. An exemplary placement of multiple electrode patches 26 on the outer surface of the inflated cuff is shown in FIG. 2. In certain embodiments, there is a plurality of sense electrodes that includes at least two sense electrodes, and preferably includes three, four or five sense electrodes. The combination of five sense electrodes provides three orthogonal pairs of sense electrodes.

The portion of the electrode runner 28 on the region of the inflatable cuff 22 that does not contact the tube is fabricated such that it forms a beam-like structure 36. By this is meant that the electrode runners on the inflatable cuff remain substantially linear and rigid when the inflatable cuff is 22 deflated. These beam-like structures 36 are important to the functionality of the apparatus 10 when it is inserted into a subject because they increase electrode durability and facilitate deflation of the inflatable cuff 22. When the distal portion 16 of the tube 12 is placed in a subject's trachea and the inflatable cuff 22 is inflated to secure the apparatus in position, the electrode patches 26 come into tight contact with the subject's tracheal walls. During the breathing cycle, the pressure on the inflated cuff 22 rhythmically increases and is then relaxed. The beam-like structures 36 do not appreciably change shape during this cycle, but there is substantial change in the shape of the portions of the inflatable cuff between the beam-like structures 36, which decreases the force on the beam-like structures 36 and increases durability of the electrodes.

The regions of the electrode runners 28 that are positioned on the inflatable cuff 22 are arranged in an array so as to increase the ability of the cuff 22 to collapse when deflated, such that the electrode patches and beam-like structures 36 lay roughly flat against the portion of the tube underlying the inflatable cuff 22. In certain embodiments, multiple beam-like structures 36 extend from the point where the proximal end 38 of the inflatable cuff 22 contacts the tube to the electrode patch.

The electrode runners 28 are placed generally parallel to adjoining electrode runners along the distal portion of the tube. The width of the electrode runner 28 can by adjusted. For example, the width of the electrode runner 28 can range from about 0.1 millimeters to about two millimeters; in a preferred embodiment, the electrode runners 28 are about one millimeter in width along the distal portion of the tube 12. The electrode runners 28 diverge from adjoining electrode runners 28 at a point on the tube proximal to the inflatable cuff 22; in other words, the distance between adjacent runners 28 is generally uniform along the length of the distal portion 16 of the tube 12, but increases as the electrode runners 28 near the inflatable cuff 22. The electrode runners 28 extend generally linearly along the surface of the inflatable cuff 22 to form beam-like structures 36 and separate from adjacent beam-like structures 36. This separation increases as the electrode runners 28 approach the electrode patches 26, which are in proximity to the point of the inflatable cuff 22 at which the maximal circumference 40 is obtained. The result of this separation is that the circumferential distance between adjacent beam-like structures 36 is greater at the region of the inflated inflatable cuff wherein maximal outer diameter 40 of the cuff 22 is achieved than at the region where the inflatable cuff 22 contacts the distal portion 16 of the tube 12. This separation increases the ability of the electrode patches 26 and beam-like structures 36 to fold flat against the tube 12 during deflation of the inflatable cuff 22.

The apparatus 10 also includes a current electrode 42. The current electrode 42 has an electrode patch 44 of generally rectangular shape that is positioned between the distal end of the tube 12 and the midpoint 46 of the apparatus. Preferably, the current electrode 42 is located on the outer radius of the curve formed by the tube. This orientation provides for better contact between the current electrode 42 and the subject's trachea. The current electrode 42 is of an area sufficient to function as a current electrode. For example, the electrode patch 44 of the current electrode 42 is at least 28 millimeters in length as measured in a proximal-distal orientation. The current electrode 42 also includes an electrode runner 48 extending distally from the flex circuit 30 of the apparatus to the electrode patch 44 of the current electrode 42. In some embodiments the current electrode extends over about 90°, 120°, or about 180°. of the circumference of the tube. As described herein, the current electrode runner 48 is fabricated from a conductive material, and is separated from the tube 12 by a polymeric underlayer 77 that is applied to the tube 12 prior to application of the conductive material. The electrode patch of the current electrode 44 may be separated from the tube 12 by the polymeric underlayer 77. Furthermore, the current electrode runner 48 is covered by a polymeric overlayer applied to the conductive material.

When fully inflated, the cuff 22 is of sufficient size to fix the position of the endotracheal tube such that there is not substantial movement either downward or upward relative to the subject's trachea. For example, the cuff 22 has a maximal outer diameter of at least twenty millimeters.

In certain embodiments the apparatus also includes a tubule 24 for inflating the inflatable cuff 22. For example, the tubule 24 has a proximal 50 and distal end 52, the distal end 52 extending from the cuff 22 in the internal space of the distal portion 16 of the tube 12 and exiting the tube 12 in the proximal portion 14 near the midline 46. The proximal end 50 of the tubule has an inlet 54 for air or another gas under pressure for inflating the cuff 22. At the proximal end 50 of the tubule 24 is a valve housing provided with an air inlet bore 56 and valve means 58 in the bore 56 such that the inlet is 54 normally closed, but air is admitted under pressure through the inlet bore 56 to inflate the cuff 22.

In certain embodiments, the apparatus 10 is operably connected to a bioelectrical impedance recorder, where the impedance recorder is electrically coupled to the sense electrodes. Bioelectrical impedance analysis of blood flow using electrode sensors arrayed within or external to the trachea is well known in the art. See, e.g., U.S. Pat. Nos. 5,791,349 and 6,095,987, the contents of which are incorporated herein by reference in their entireties.

Figure 4:
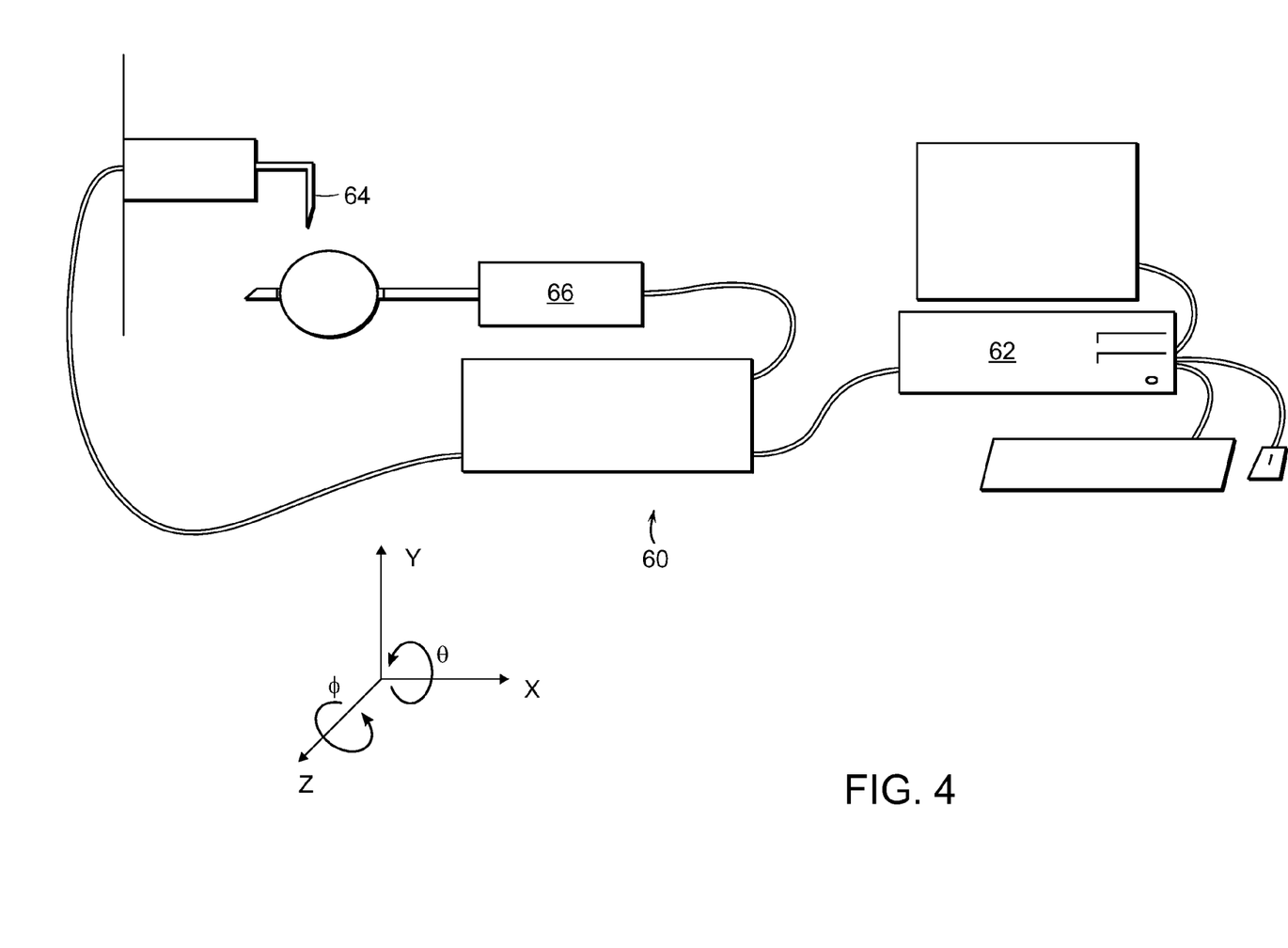
FIG. 4 is a schematic illustration of a positive displacement dispensing system used in the present invention.

Fabrication of Electrodes on Endotracheal Tubes Using a Positive Displacement Dispensing System In certain embodiments the present invention provides an apparatus 10 arrayed with electrodes 26, 28 disposed on an inflatable cuff 22. These electrodes 26, 28 are applied to the tubes 12 using a novel printing methodology that uses a positive displacement dispensing system 60. While this methodology is specifically described herein as useful for applying materials onto the surface of the apparatus 10 and the associated inflatable cuff 22, one of skill in the art will recognize that the printing methods described herein are also useful for applying a material to any non-repeatably formed substrate (e.g., a dilation balloon used in a medical device).

The printing methodology generally involves two steps: imaging the non-repeatably formed substrate and applying one or more materials thereon. The application step can be termed "writing", "printing" or any other equivalent term known to those skilled in the art. These two general steps are discussed in turn.

The inflatable cuff 22 is at least partially inflated prior to printing the electrodes 26, 28 on its outer surface. Due to inherent variations in the three dimensionality of the inflated cuff 22 one must have an understanding of the shape of the inflated cuff 22 prior to positioning the electrodes 26, 28. For this reason, the inflated cuff is 22 imaged by capturing either video or still images. In certain embodiments video images of the inflated cuff 22 and the adjacent regions of the distal region 16 of the tube 12 are collected and sent to a processing system, such as a computer 62 that generates a map showing the contours of the inflated cuff 22. In other embodiments, one or more still images are captured and reproduced (such as by digital printing) in order to generate the contour image map. Generally three or more still images are captured to generate the contour image map. In preferred embodiments, eight images are captured.

Information from the contour map obtained above is provided to a positive displacement dispensing system 60 capable of responding to the contour map by altering one or more printing dimensions. The displacement dispensing system contains a writing head 64 (such as a pen tip) and a substrate stage 66 capable of moving the substrate in at least three independent dimensions. The writing head is 64 capable of movement relative to the substrate stage 66. The writing head 64 applies to the substrate any liquid or semi-solid materials, including the polymeric underlayer and overlayers, and the conductive material used to form the electrodes 26, 28.

An exemplary positive displacement dispensing system 60 is shown in FIG. 4. A writing head 64 is mounted on an axis capable of moving in one dimension only, shown in FIG. 4 as the y-axis. In contrast, the substrate stage 66 is capable of moving in at least three independent dimensions, shown in FIG. 4 as the x-axis, φ (clockwise or counter-clockwise rotation along the z-axis, and θ (clockwise or counter-clockwise rotation along the x-axis). In certain embodiments, the substrate stage 66 is capable of moving in a fourth independent direction, shown in FIG. 4 as the y-axis.

Preferably, the positive displacement dispensing system 60 is used to print the electrodes 26, 28 in a sandwich format: the conductive material is surrounded by the polymeric underlayer 77 on the bottom (i.e., the area closest to the tube 12) and the polymeric overlayer on the top (i.e., the area furthest from the tube 12), except for a portion of the electrode patch 26, which is not covered by the polymeric overlayer and therefore is able to directly contact the tracheal mucosa when inserted into a subject's trachea, and the end of the electrode runner 28 that contacts the external wires 30. As such, the writing head 64 applies to a region of the inflated cuff 22 a polymeric underlayer 77. The region to which the polymeric underlayer 77 is applied is based upon the imaging data obtained from the contour map described above. Extending from the flex circuit 30 of the apparatus 10 the writing head 64 writes a thin, narrow layer of material directly on the distal portion 16 of the tube 12 and extending to the inflatable cuff 22, which is at least partially inflated. For example, the inflatable cuff 22 is inflated to an inflation pressure of about 10 to about 40 cm H$_2$O, e.g., about 25 cm H$_2$O. Because the course of the writing head 64 is controlled based on information regarding the contours of the inflated cuff 22 and the distal portion 16 of the tube 12, multiple parallel lines can be formed along the proximal-distal axis of the tube 12. As used herein, materials useful as polymeric underlayer 77 include an ultraviolet (UV)-curable resin such as Dymax®0 1-20323 resin and Creative Materials dielectric inks (e.g., CMI-115-30). Prior to printing the underlayer 77 the tube 12 and cuff 22 may be cleaned with a solvent such as ethanol or with physical means (such as an ionizing gun) to remove debris. After printing, the underlayer 77 is optionally cured, such as by exposure to UV or visible light radiation or a similar curing agent.

Wrinkles or other deformations may exist in the cuff 22 prior to printing. In certain embodiments, prior to printing the underlayer the tube 12 may be heated, such as at 30-100° C. (e.g., about 60° C.) for a period of time (e.g., 1-60 minutes, preferably about 45 minutes) after inflation of the cuff 22 to remove any wrinkles present in the tube 12 or the inflatable cuff 22. Alternatively, a physical force can be applied to the cuff 22 to remove any wrinkles prior to printing.

The shape of the inflatable cuff 22 can be modified prior to electrode printing. For example, a vacuum can be applied to the end of the cuff 22 closest to the distal tip 18 of the apparatus, resulting in a deformation of the cuff 22; this deformation preferably results in a decrease in the angle formed by the inflatable cuff 22 as it extends away from the proximal end of the tube, such that printing on the cuff becomes easier.

In certain embodiments, physical force can be applied to the proximal end 38 of the cuff 22 by contacting one or more regions of the cuff with projections, or "fingers", that pull the cuff in a distal direction along a proximal-distal axis. The printing of the electrode patches 26 and electrode runners 28 is performed by applying the writing head 64 with the portions of the inflatable cuff 22 not contacted or otherwise obscured by the projections. The application of physical force reduces or eliminates any wrinkles in the inflatable cuff 22 and transforms the inflatable cuff 22 into a defined writing surface, thereby obviating the need to image the inflated cuff 22 prior to the writing step.

Upon completion of the printing of the polymeric underlayer 77, the dispensing system 60 has a functional "road map" for where to place the conductive material that is used to form the electrode runners 28 and electrode patches 26. Generally, the width of the line formed by the conductive material will be less than that of the polymeric underlayer 77, such that no conductive material directly contacts either the distal portion 16 of the tube 12 or the inflatable cuff 22. As used herein, materials useful as a conductive material include electrically conductive inks such as CMI 101-59 (Creative Materials Inc., Tyngsboro, Mass.) or any other electrically conductive particles such as silver or gold particles that are suspended in a resin and a solvent. After printing the conductive material on the tube 12 is optionally cured, such as by heating the tube. This curing step results in the formation of a polymeric matrix surrounding the conductive particles. By way of non-limiting example, the tube 12 is placed in a suitable container, which is then heated to a temperature of 90-150° C. (e.g., 120° C.) for a period of time (e.g., 30 minutes to five hours or more). The temperature of the container may be gradually increased, such as increasing the temperature by 0.1-5° C. per minute.

A polymeric overlayer 76 is written over the conductive material the length of the electrode runner 28, which is acceptable because no signals are directly measured from the electrode runner 28 itself. The overlayer is written over the outer periphery of the electrode patch 26 on the inflated cuff 22. For example, the outer one millimeter of each side of the electrode patch 26 is covered with the polymeric overlayer. The purpose of this overlayer is to increase durability of the electrodes 26, 28 and prevent errors in signal processing. Additionally, in one embodiment the overlayer extends from the periphery of the electrode patch 26 over the polymeric underlayer 77 and onto the surrounding material of the inflatable tube 22. In another embodiment, the overlayer extends beyond the periphery of the electrode patch 26 but does not extend beyond the polymeric underlayer 77. This extension results in a seal that strengthens the attachment of the electrode patch 26 to the inflatable tube 22, thereby decreasing the probability that physical strain on the electrode patch 26 will cause its separation from the inflatable tube 2.

As used herein, materials useful as polymeric overlayers include an ultraviolet (UV)-curable resin such as Dymax® 1-20323 resin, or Creative Materials dielectric ink (e.g., CMI-115-30). Prior to printing the overlayer, the tube 12 may be cleaned with a solvent such as ethanol or with physical means (such as an ionizing gun) to remove debris. After printing the overlayer the apparatus 10 is optionally cured, such as by exposure to UV or visible light radiation or a similar curing agent.

Measurement of Cardiac Output

Endotracheal tubes bearing electrodes have been previously described as useful for measuring cardiac function, including cardiac output. See U.S. Pat. Nos. 6,095,987 and 6,292,689. The endotracheal tubes as described herein are useful to measure physiological functions in mammalian subjects. For example, cardiac output is measured, and any pathological situation identified, using the electrodes arrayed on the inflatable cuff. Thus, the invention provides a method of measuring the cardiac output of a mammalian subject by providing an endotracheal tube substantially as described herein. The endotracheal tube includes a current electrode connected thereto and an inflatable cuff containing an array of electrodes including a plurality of sense electrodes and a ground electrode, and is positioned in the trachea in the vicinity of the aorta so that inflating the cuff results in the cuff contacts the tracheal mucosa. Once the inflatable cuff is positioned, a current is injected into the subject's trachea through the current electrode, a voltage is established between the current electrode and the ground electrode so that a current flows through the tissue disposed between the current electrode and the ground electrode. With one or more sense electrodes the voltages caused by the current flowing in the tissue is detected, wherein the voltages vary in accordance with changes in the bioelectrical impedance of the tissue. Generally, the tube is adapted to be inserted in the trachea of the subject through the mouth, a nasal passageway, or a tracheotomy port.

The present invention is not limited to the particular methodologies, protocols, constructs, formulae and reagents described but further include those known to the skilled artisan. It is also to be understood that the terminology used herein is for the purpose of describing particular embodiments only, and is not intended to limit the scope of the present invention.

Unless defined otherwise, all technical and scientific terms used herein have the same meaning as commonly understood to one of ordinary skill in the art to which this invention belongs. Any methods, devices, and materials similar or equivalent to those described herein can be used in the practice or testing of the invention. All publications and patents mentioned herein are incorporated herein by reference.

What is claimed is:

1. A medical device comprising:
   a tube having a proximal portion and a distal portion;
   an inflatable cuff connected to the distal portion of said tube; and
   a plurality of sense electrodes, each of said sense electrodes comprising,
   an electrode patch joined to said inflatable cuff,
   an electrode runner extending a length in a proximal-distal orientation from said electrode patch, along said inflatable cuff, and along said distal portion of said tube, said electrode runner being joined along the length to said inflatable cuff and said tube,
   a polymeric underlayer applied on the inflatable cuff and the tube, the polymeric underlayer separating said electrode patch from said inflatable cuff and separating said electrode runner from said inflatable cuff and said tube, and
   a polymeric overlayer applied over the length of said electronic runner and applied over a periphery of said electrode patch,
   wherein said electrode runner, said polymeric underlayer, and said polymeric overlayer being in a sandwich format with said polymeric underlayer being on the bottom and closest to said tube, said polymeric overlayer being on the top and farthest from the tube, and said electrode runner being between said polymeric underlayer and said polymeric overlayer.

2. The medical device of claim 1, wherein a circumferential distance between adjacent electrode runners is greater at a region of the inflated inflatable cuff when a maximal outer diameter of the cuff is achieved than at a region where the inflatable cuff contacts the distal portion of the tube.

3. The medical device of claim 2, wherein the polymeric overlayer is applied to said periphery of the sense electrode patches and said electrode runners after application of said sense electrode patches and said electrode runners to the tube and cuff.

4. The medical device of claim 3, wherein the polymeric underlayer comprises a UV curable adhesive, the sense electrodes comprise an electrically conductive ink, and the polymeric overlayer comprises a UV curable adhesive.

5. The medical device of claim 1, further comprising a tubule for inflating the inflatable cuff.

6. The medical device of claim 1, wherein the polymeric underlayer is applied to the inflatable cuff and the tube prior to application of the sense electrodes.

7. The medical device of claim 1, wherein the plurality of sense electrodes comprises five sense electrodes and the combination of the five sense electrodes provides three orthogonal pairs of sense electrodes.

8. The medical device of claim 7, wherein the tube is an endotracheal tube.

9. The medical device of claim 1 further comprising a current electrode joined on the distal portion of the tube approximately equidistant from a distal end of the tube and the midpoint of the tube.

10. The medical device of claim 9, wherein the current electrode is at least one centimeter in length as measured along a proximal-distal dimension of the tube.

11. The medical device of claim 1, wherein the electrode patch and the electrode runner of the sense electrodes comprise electrically conductive particles suspended in a polymeric matrix material.

12. The medical device of claim 11, wherein the electrically conductive particles are selected from silver and gold.

13. The medical device of claim 1, wherein electrode runner comprises a substantially linear and rigid beam like structure on the inflatable cuff that remains substantially linear and rigid when the inflatable cuff is deflated.

14. The medical device of claim 1, wherein the electrode patch and the electrode runner of the sense electrodes are written as a trace on the tube and/or the inflatable cuff.

* * * * *